US006883521B2

(12) United States Patent
McMichael (10) Patent No.: US 6,883,521 B2
(45) Date of Patent: Apr. 26, 2005

(54) METHOD AND APPARATUS FOR DOSING SINGLE AND MULTI-AGENT THERAPY

(75) Inventor: John P. McMichael, Wexford, PA (US)

(73) Assignee: Dimensional Dosing Systems, Inc., Nokomis, FL (US)

( * ) Notice: Subject to any disclaimer, the term of this patent is extended or adjusted under 35 U.S.C. 154(b) by 0 days.

(21) Appl. No.: 10/453,749

(22) Filed: Jun. 3, 2003

(65) Prior Publication Data

US 2003/0192560 A1 Oct. 16, 2003

Related U.S. Application Data

(63) Continuation-in-part of application No. 09/939,056, filed on Aug. 24, 2001, now Pat. No. 6,578,582.

(51) Int. Cl.$^7$ ................................................ A61B 19/00

(52) U.S. Cl. ...................................... 128/898; 600/300

(58) Field of Search .................... 128/897–98; 600/300, 600/308, 347, 364–66, 368

(56) References Cited

U.S. PATENT DOCUMENTS

| 5,365,948 A | 11/1994 | McMichael | 128/898 |
|---|---|---|---|
| 5,542,436 A | 8/1996 | McMichael | 128/898 |
| 5,694,950 A | 12/1997 | McMichael | 128/898 |
| 6,267,116 B1 | 7/2001 | McMichael | 128/898 |
| 6,575,169 B2 | 6/2003 | McMichael | 128/898 |
| 6,578,582 B2 | 6/2003 | McMichael | 128/898 |

*Primary Examiner*—John P. Lacyk
(74) *Attorney, Agent, or Firm*—Gifford, Krass, Groh, Sprinkle, Anderson & Citkowski, P.C.

(57) ABSTRACT

An improved method and apparatus using a newly defined nonlinear technology that more accurately describes the biological process of dose titration to calculate next agent dose(s) in single and multi-agent therapy. The overall proportion of each agent is determined by the amount of agent as it relates to the dosing range. The overall proportion as well as the intrinsic potency of the agent is used to determine the total proportional effect that each agent has on the surrogate marker. This parameter is then inserted into the four-parameter equation for calculating dose by adjusting the proportional change in marker that is attributed to the activity of the agent.

10 Claims, 2 Drawing Sheets

METHOD AND APPARATUS FOR DOSING SINGLE AND MULTI-AGENT THERAPY

CROSS-REFERENCE TO RELATED APPLICATIONS

This application is a continuation-in-part of U.S. patent application Ser. No. 09/939,056, which was filed on Aug. 24, 2001 now U.S. Pat. No. 6,578,582.

This document may contain material that is the subject of copyright protection. All rights in such copyrightable material are hereby reserved.

FIELD OF THE INVENTION

The present invention relates generally to a method and apparatus using a newly defined nonlinear technology for multi-agent therapy. More particularly, the present invention relates to a method and apparatus for use in treating a patient with a single or multiple agents to optimize therapy and to prevent an adverse response. The present invention can utilize either biological substance levels or other surrogate markers to determine the effectiveness of the dosing regimen and, if necessary, to suggest a new more optimal regimen.

The term "agent" as used herein includes, but is not limited to: vaccines; serums; drugs including but not limited to antibiotics, anti-virals, immunosuppressants, anticoagulants; adjuvants to enhance or modulate a resulting immune response; vitamin antagonists; medications; autologous whole-cell vaccines (using cells derived from a patient's own tumor); allogenic whole-cell vaccines (using cancer cell lines established in vitro and then used to vaccinate multiple patients); tumor specific antigen/tumor associated antigen (TSA/TAA) based vaccines and hormonal autoimmunization approaches; all other cancer vaccines; Melacine; CancerVax; immune-boosting interferon; peptides; dendritic cells having melanoma protein thereon; interleukin-12; substances which stimulate or energize blood cells known as CD8 T cells; genes which make interleukin-12; tumor cells weakened by genes which make interleukin-12; substances which block blood-vessel formation to prevent growth of tumors; immunized cells; recombinant subunit vaccines; DNA vaccines; live recombinant viral vector vaccines; live recombinant bacterial vector vaccines; live-attenuated vaccines; whole-inactivated vaccines; virus-like particle vaccines; synthetic peptide vaccines; "Jennerian" vaccines; complex vaccines; and combinations of two or more of the foregoing.

The term "surrogate marker" as used herein means all surrogate markers and includes, but is not limited to: a measurement of biological activity within the body which indirectly indicates the effect of treatment on a disease state or on any condition being treated; and any measurement taken on or of a patient which relates to the patient's response to an intervention, such as the intervention of a biological substance introduced into or on the patient. For example, CD4 cell counts and viral load are examples of surrogate markers in HIV infection.

BACKGROUND OF THE INVENTION

When a patient begins taking an agent or combination of agents or any medication(s) for a length of time, a titration of the amount of agent(s) taken by the patient is necessary in order to achieve the optimal benefit of the agent(s), and at the same time to prevent any undesirable side effects that taking too much of the agent(s) could produce. Thus, there is a continuous balance between taking enough of the agent(s) in order to gain the benefits from that agent(s), and at the same time not taking so much agent(s) as to elicit a toxic event.

There is large inter-individual variability in the patient biological interactions and/or the patient pharmacodynamic and pharmacokinetic interactions of agents. What may be an appropriate agent dose for one individual may be too much or too little for another. A physician referring to the product insert is required to estimate the correct agent dosage for a patient and then to experiment with that dosage, usually by trial and error, until the correct dosage is achieved. Likewise, the FDA labeling of an agent suggests dosages based on epidemiological studies and again does not account for inter-individual variability. Non-linear least squares modeling methods involve the use of large amounts of data relating to a general population in order to calculate a best fit. Much like linear regression models, this method cannot take into account the variability between people with the same population characteristics.

Bayesian analysis is another method used to relate agent dose to efficacy. This method employs large-scale population parameters to stratify a population in order to better characterize the individuals. This method does not take into account the changes that can occur within a person over time, and as a result cannot reliably estimate dosages.

Pharmacokinetic compartment modeling has had success with some agents, but because the models are static and cannot adapt themselves to changes within a population or a patient, they are once again undesirable for dynamically determining agent dosages.

Expert systems have been developed by this applicant using similar technology to predict drug dosages for immunosuppressant drugs (U.S. Pat. Nos. 5,365,948; 5,542,436 and 5,694,950). These algorithms however were not generic and only use immunosuppressant blood levels. Each algorithm is specific to an individual immunosuppressant drug. As it stands, these inventions cannot be applied to other drugs. A more recent dosing system, the IDS™ has been developed (U.S. Pat. No. 6,267,116 B1) that is generic but does not take into account the level or degree of response that a patient has. Some biological markers cannot be pushed beyond certain limits such as the INR, blood pressure or glucose levels. This system (U.S. Pat. No. 6,267,116 B1) also only produces a single next dose as its calculation. The system being described produces the range of doses necessary to achieve the desired response, plus or minus 5%. This is clinically much more relevant to the physicians treating their patients. This model also requires a separate embodiment for the percentage of surrogate markers embodiment that is not required in this new model. Previous dosing models put forth by the applicant assumed that the degree of nonlinearity continually increased over the dosing range. These models did not take into account the saturation effect that high doses of drug exhibit, that is where the degree of nonlinearity begins to decrease at the highest end of the dosing range. Saturation of response occurs as more and more drug is added to a system. While more drug elicits a larger effect, at very high doses the effect is lessened due to the inability to push biological markers beyond certain limits. The dosing model set out in this application more accurately describes and takes into account the saturation effect as it relates to the biological process of dose titration.

Applicant's U.S. Pat. No. 6,267,116 discloses a major breakthrough in IDS™ technology, but can only accommodate one drug at a time and is inferior dosing technology for the reasons described above.

It is a desideratum of the present invention to avoid the animadversions of conventional systems and techniques.

SUMMARY OF THE INVENTION

The present invention provides in one embodiment thereof a method of calculating the best next dose for each agent of a single or multi-agent therapy which a patient may be using, comprising the steps of: accepting as first inputs the patient's current dose(s) of a single or plurality of agents which the patient may be using; accepting as second inputs one or more numerical markers indicating one or more responses of the patient; and calculating new agent dose(s) for said agent or plurality of agents as a function of said first inputs, said second inputs, and contributions which each agent makes to an overall effect to be achieved by said multi-agent therapy.

The present invention provides in a further embodiment thereof a storage device having stored thereon an ordered set of instructions which, when executed by a computer, performs a predetermined method, comprising: first means for accepting as first inputs a patient's current doses of a plurality of agents which the patient may be using; second means for accepting as second inputs one or more numerical markers indicating one or more responses of the patient; and third means for calculating new agent doses for said plurality of agents as a function of said first inputs, said second inputs, and contributions which each agent makes to an overall effect to be achieved by said multi-agent therapy.

The present invention provides in another embodiment thereof an apparatus for calculating the next best dose for each agent of a multi-agent therapy which a patient may be using, comprising: first means for accepting as first inputs the patient's current doses of a plurality of agents which the patient may be using; second means for accepting as second inputs one or more numerical markers indicating one or more responses of the patient; and third means for calculating new agent doses for said plurality of agents as a function of said first inputs, said second inputs, and contributions which each agent makes to an overall effect to be achieved by said multi-agent therapy.

DETAILED DESCRIPTION OF THE PREFERRED EMBODIMENTS

Figure 1:
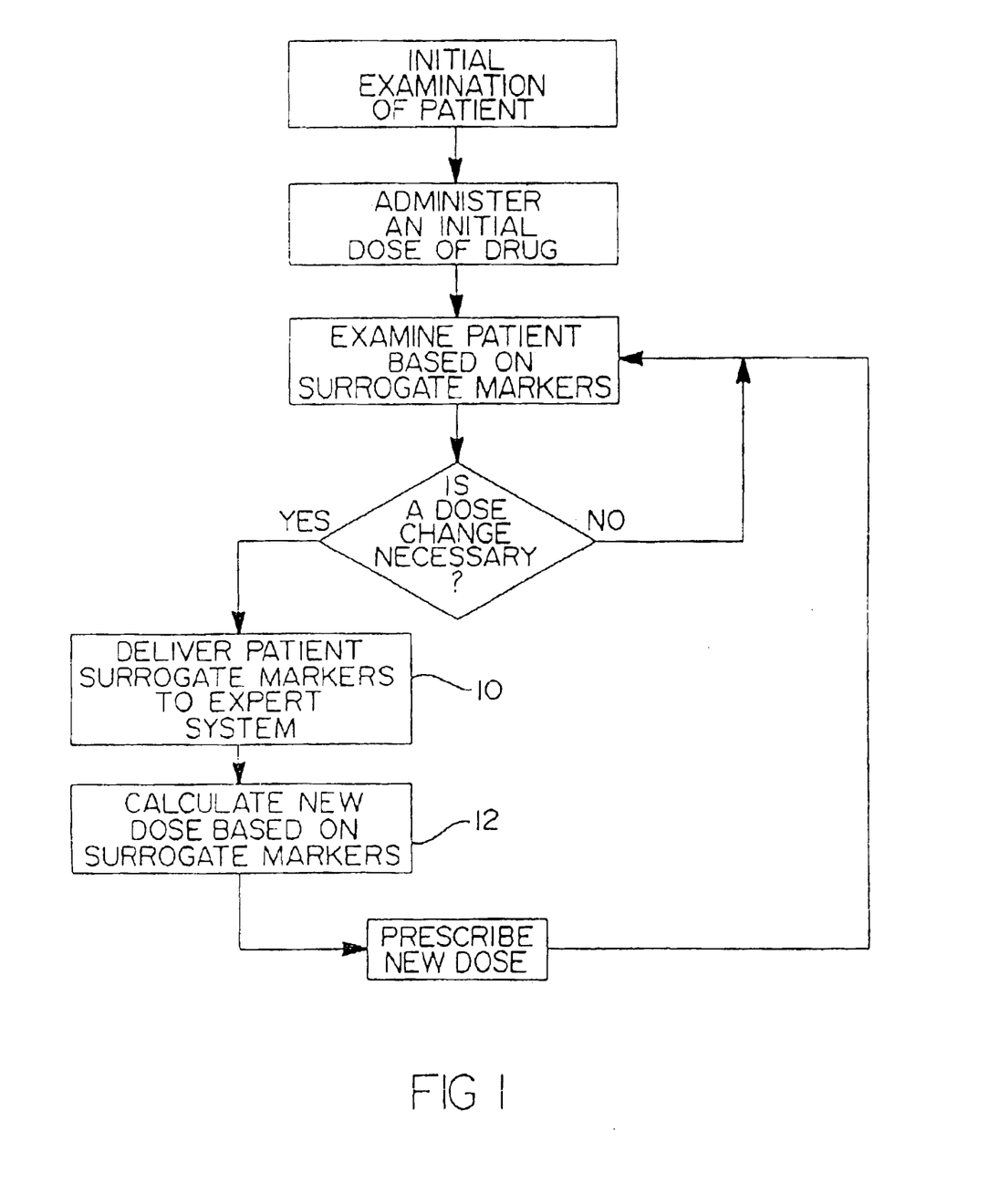
FIG. 1 shows a flowchart of the process by which new doses of an agent, of a multi-agent therapy, are determined according to a portion of the method of the invention.

FIG. 1 shows a flowchart of a portion of the overall process of treating a patient using this expert system. The actual expert system performs many steps that are described herein, whereas only the steps shown in blocks 10 and 12 are generally indicated the flowchart.

Figure 2:
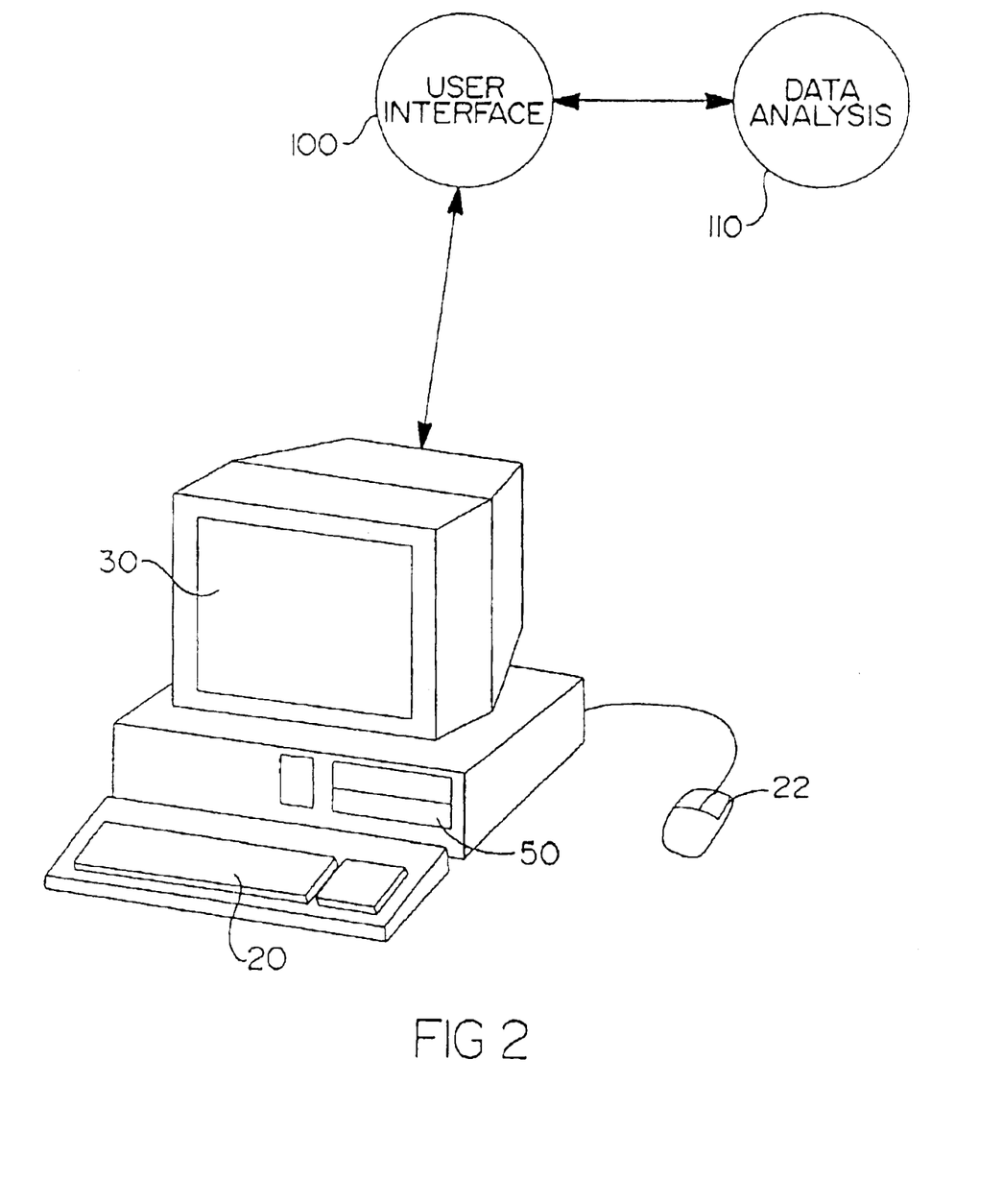
FIG. 2 shows an apparatus for use in calculating new doses of a plurality of agents used in a multi-agent therapy according to the invention.

This expert system includes a general purpose computer, shown in FIG. 2, comprising an input means, preferably a keyboard/text/voice entry device 20 and/or a mouse/pointing/tapping/visual pointing device 22, an output means 30, preferably a video display screen, a data storage means 50, preferably a hard disk drive or non-volatile storage medium, and a processor. The expert computer program receives input from a physician regarding the patient's current drug dose, the doseslope50 value for the drug, the percent response of the patient based on the surrogate markers used to monitor the drug. The doseslope50 value represents the amount of drug a typical patient is on when a 50% change in drug dose results in a 25% change in response or when there is half as much percent response as there is dose change. The embodiment of this invention requires that a physician determine the percentage of response by the patient to the drug based on the surrogate markers for that drug. A relationship is then employed which uses the input parameters described above to determine the next dose for the patient. This invention has two embodiments, one which uses actual numerical surrogate markers to calculate a dose and another embodiment that uses percentages as the numerical input for the surrogate markers.

The software portion of the invention includes a user interface portion 100 to receive the input data and to output the revised dosage information, and a data analysis portion 110, which calculates the new dosage information based on the input data.

A physician prescribes an agent for a patient based on the FDA recommended dose on the label of the agent. The physician then reevaluates the patient, usually daily, either in person or remotely depending on the agent being prescribed.

During the subsequent evaluations by the physician, the surrogate marker or markers are monitored and sequentially compared to determine if there are any toxicities associated with the agent. Also the numerical markers will be evaluated to see if the desired effect of the agent is being achieved.

Given the effectiveness of the agent's action relative to the surrogate markers, a change in agent dose is calculated by the system. Conversely, by employing this system, one could determine the expected result of the agent dose change on the surrogate marker.

The present invention will now be described in detail with respect to 2-agent therapy and 3-agent therapy, although it is applicable to any number (n-agents) of agents.

Single-agent (1 Agent) Therapy

Patient dosing typically follows a cyclic series of events (FIG. 1). A drug (therapeutic agent) is prescribed by a physician for a patient, the initial dose is based on the FDA recommended dosage found on the drug label. The drug dose is further refined upon repeated dosing by the physician based on the patient's response to the drug. Too much drug and the patient could experience toxic drug effects and the drug dose would need to be reduced. Too little drug and the patient would not receive the benefit the drug therapy could offer and the dosage would need to be increased. This expert system includes a general-purpose computer comprising an input means, an output means, a data storage means and a processor. The expert computer program receives input from a physician regarding the patient's current drug dose, the percent response of the patient based on the surrogate markers used to monitor the drug. The embodiment of this invention requires that a physician determine the percentage of response by the patient to the drug based on the surrogate markers for that drug. A relationship is then employed which uses the input parameters described above to determine the next dose for the patient. This invention has two embodiments, one that uses actual numerical surrogate markers to calculate a dose and another embodiment that uses percentages as the numerical input for the surrogate markers.

The generic relationship has the following embodiment as follows:

To Calculate the Dose for One Agent $$NDD = CDD + ((\% \text{ change level}/MF))/1 + (CDD/DrugRange)) * CDD$$

Wherein,
% change level=(DDNM−CDNM)/CDNM For regular markers
% change level=(CDNM−DDNM)/CDNM For inverse markers
NDD=New Drug Dose
CDD=Current Drug Dose
CDNM=Current Drug Numerical Marker
DDNM=Desired Drug Numerical Marker
MarkerFunction (MF)=1.5^ (CDNM/MarkerRange)
MarkerRange=The maximal range typically seen for the marker.
DrugRange=The maximal range typically prescribed for the drug.

To Calculate the Level/Response for One Agent $$NDL = -1 * CDL * ((NDD * MF * DrugRange + NDD * MF * CDD * MF * DrugRange - 1 * CDD\textasciicircum 2 * MF - 1 * DrugRange * CDD)/(DrugRange * CDD))$$

Wherein,
NDL=New Drug Level
NDD=New Drug Dose
CDL=Current Drug Level
CDD=Current Drug Dose
MarkerFunction (MF)=1.5^ (CDNM/MarkerRange)
MarkerRange=The maximal range typically seen for the marker.
DrugRange=The maximal range typically prescribed for the drug.

Multi-agent (2 Agents) Therapy

When using a multi-agent regimen to treat patients it is necessary to calculate the next best dose for each agent the patient is using. This technology in the form disclosed in applicant's U.S. Pat. No. 6,267,116 can only dose one agent at a time and requires previous dosing experience to individualize and improve dosing accuracy. The following calculations show how to use the concept of the dosing technology described herein and the dose response methodology to perform multiple computations, each based on the proportional response that a particular agent has on the overall response that is to be achieved.

The concept underlying this multi-agent dosing model is that each agent has some contribution to the overall effect. This contribution is determined by the amount of each agent the patient is using as well as the intrinsic potency of each agent. The overall proportion of each agent is determined by the amount of agent as it relates to the dosing range. The overall proportion as well as the intrinsic potency of the agent is used to determine the total proportional effect that each agent has on the surrogate marker. This parameter (FOE1 or FOE2) is then inserted into the four-parameter equation (NAD) for calculating dose by adjusting the proportional change in marker that is attributed to the activity of the agent.

To Calculate the Dose for the First Agent $$NAD1 = CAD1 + (\% \text{ change level First}/MF)/1 + (CAD1/DrugRange1)) * CAD1$$

To Calculate the Dose for the Second Agent $$NAD2 = CAD2 + (\% \text{ change level Second}/MF)/1 + (CAD2/DrugRange2)) * CAD2$$

Wherein:

% change level First=(DDNM−CDNM)*FOE1/CDNM For regular markers
% change level First=(CDNM−DDNM)*FOE1/CDNM For inverse markers
% change level Second=(DDNM−CDNM)*FOE2/CDNM For regular markers
% change level Second=(CDNM−DDNM)*FOE2/CDNM For inverse markers
CAD1=Current agent dose of the first agent
CAD2=Current agent dose of the second agent
NAD1=New first agent dose value
NAD2=New second agent dose value
CDNM1=Current agent numerical marker for the first agent
CDNM2=Current agent numerical marker for the second agent
DDNM1=Desired agent numerical marker for the first agent
DDNM2=Desired agent numerical marker for the second agent
FOE1=Factor of effect the first agent has on its associated numerical marker
FOE2=Factor of effect the second agent has on its associated numerical marker
MarkerFunction (MF)=1.5^ (CDNM/MarkerRange)
MarkerRange=The maximal range typically seen for the marker.
DrugRange1=The maximal range typically prescribed for drug1.
DrugRange2=The maximal range typically prescribed for drug2.

To Calculate the Level/Response for the First Agent $$NDL1 = -1 * CDL * ((NDD1 * MF * DrugRange1 + NDD1 * MF * CDD1 * MF * DrugRange1 - 1 * CDD1\textasciicircum 2 * MF - 1 * DrugRange1 * CDD1)/(DrugRange1 * CDD1))$$

To Calculate the Level/Response for the Second Agent $$NDL2 = -1 * NDL1 * ((NDD2 * MF * DrugRange2 + NDD2 * MF * CDD2 * MF * DrugRange2 - 1 * CDD2\textasciicircum 2 * MF - 1 * DrugRange2 * CDD2)/(DrugRange2 * CDD2))$$

Wherein,

NDL1=New First Drug Level
NDL2=New Second Drug Level
CDL=Current Drug Level
MarkerFunction1(MF1)=1.5^ (CDL/MarkerRange)
MarkerFunction2(MF2)=1.5^ (CDL/MarkerRange)
MarkerRange=The maximal range typically seen for marker.
DrugRange1=The maximal range typically prescribed for the drug1.
DrugRange2=The maximal range typically prescribed for the drug2.

To Calculate the Proportion of Effect Based on the Amount of Agent and the Agent's Intrinsic Effect Agent1 Effect=1
Agent2 Effect=1

$$Agent1\ Proportion = \frac{Dose1/Range1}{(Dose1/Range1 + Dose2/Range2)}$$

$$Agent2\ Proportion = \frac{Dose2/Range2}{(Dose1/Range1 + Dose2/Range2)}$$

$$FOE1 = \frac{Dose1/Range1}{(Dose1/Range1 + Dose2/Range2)} \times Agent1\ Effect$$

$$FOE2 = \frac{Dose2/Range2}{(Dose1/Range1 + Dose2/Range2)} \times Agent2\ Effect$$

EXAMPLE 1

Gemzar Dose is 5000
Taxol Dose is 250
Assume Both Agents have an Equal Effect.
Current Marker (ANC) is 0.5
Desired Marker (ANC) is 1.8

$$Taxol\ Proportion = \frac{250/50}{(250/500 + 5000/3300)}$$
$$= \frac{0.5}{2.0152}$$
$$= 0.2481$$

$$Gemzar\ Proportion = \frac{5000/3300}{(250/500 + 5000/3300)}$$
$$= \frac{1.5152}{2.0152}$$
$$= 0.7519$$

$$FOE1 = \frac{250/500}{(250/500 + 5000/3300)} \times 1 = 0.2481$$

$$FOE2 = \frac{5000/3300}{(250/500 + 5000/3300)} \times 1 = 0.7519$$

Using Multi-agent (3 Agents) Therapy

When using a multi-agent regimen to treat patients it is necessary to calculate the next best dose for each agent the patient is using. The IDS™ technology in the form disclosed in applicant's U.S. Pat. No. 6,267,116 can only dose one agent at a time. The following calculations show how to use the concept of the IDS™ and the dose response methodology to perform multiple computations, each based on the proportional response which a particular agent has on the overall response that is to be achieved.

The concept underlying this multi-agent dosing model is that each agent has some contribution to the overall effect. This contribution is determined by the amount of each agent the patient is using as well as the intrinsic potency of each agent. The overall proportion of each agent is determined by the amount of agent as it relates to the dosing range. The overall proportion as well as the intrinsic potency of the agent is used to determine the total proportional effect which each agent has on the surrogate marker. This parameter (FOE1, FOE2, or FOE3) is then inserted into the four-parameter equation (NAD) for calculating dose by adjusting the proportional change in marker that is attributed to the activity of the agent.

To Calculate the Dose for the First Agent $NAD1=CAD1+(\%\ change\ level\ First/MF)/1+(CAD1/DrugRange1))*CAD1$ To Calculate the Dose for the Second Agent $NAD2=CAD2+(\%\ change\ level\ Second/MF)/1+(CAD2/DrugRange2))*CAD2$ To Calculate the Dose for the Third Agent $NAD3=CAD3+(\%\ change\ level\ Third/MF)/1+(CAD3/DrugRange3))*CAD3$ where:
% change level First=(DDNM−CDNM)*FOE1/CDNM For regular markers
% change level First=(CDNM−DDNM)*FOE1/CDNM For inverse markers
% change level Second=(DDNM−CDNM)*FOE2/CDNM For regular markers
% change level Second=(CDNM−DDNM)*FOE2/CDNM For inverse markers
% change level Third=(DDNM−CDNM)*FOE3/CDNM For regular markers
% change level Third=(CDNM−DDNM)*FOE3/CDNM For inverse markers
CAD1=Current agent dose of the first agent
CAD2=Current agent dose of the second agent
CAD3=Current agent dose of the third agent
NAD1 high First=New first agent high dose range value
NAD2 high Second=New second agent high dose range value
NAD3 high Third=New third agent high dose range value
CDNM1=Current agent numerical marker for the first agent
CDNM2=Current agent numerical marker for the second agent
CDNM3=Current agent numerical marker for the third agent
DDNM1=Desired agent numerical marker for the first agent
DDNM2=Desired agent numerical marker for the second agent
DDNM3=Desired agent numerical marker for the third agent
FOE1=Factor of effect the first agent has on its associated numerical marker
FOE2=Factor of effect the second agent has on its associated numerical marker
FOE3=Factor of effect the third agent has on its associated numerical marker To Calculate the Level/Response for the First Agent $NDL1=-1*CDL*((NDD1*MF*DrugRange1+NDD1*MF*CDD1*MF*DrugRange1-1*CDD1^2*MF-1*DrugRange1*CDD1)/(DrugRange1*CDD1))$ To Calculate the Level/Response for the Second Agent $NDL2=-1*NDL1*((NDD2*MF*DrugRange2+NDD2*MF*CDD2*MF*DrugRange2-1*CDD2^2*MF-1*DrugRange2*CDD2)/(DrugRange2*CDD2))$ To Calculate the Level/Response for the Third Agent $NDL3=-1*NDL2*((NDD3*MF*DrugRange3+NDD3*MF*CDD3*MF*DrugRange3-1*CDD3^2*MF-1*DrugRange3*CDD3)/(DrugRange3*CDD3))$ Wherein,
NDL1=New First Drug Level
NDL2=New Second Drug Level
NDL3=New Third Drug Level CDL=Current Drug Level
MarkerFunction1 (MF1)=1.5^ (CDL/MarkerRange)
MarkerRange=The maximal range typically seen for marker.
DrugRange1=The maximal range typically prescribed for the drug1.
DrugRange2=The maximal range typically prescribed for the drug2.
DrugRange3=The maximal range typically prescribed for the drug3.
To Calculate the Proportion of Effect Based on the Amount of Agent and the Agent's Intrinsic Effect
Agent1 Effect=1
Agent2 Effect=1
Agent3 Effect=1

$$Agent1\ Proportion = \frac{Dose1/Range1}{(Dose1/Range1 + Dose2/Range2 + Dose3/Range3)}$$

$$Agent2\ Proportion = \frac{Dose2/Range2}{(Dose1/Range1 + Dose2/Range2 + Dose3/Range3)}$$

$$Agent3\ Proportion = \frac{Dose3/Range3}{(Dose1/Range1 + Dose2/Range2 + Dose3/Range3)}$$

$$FOE1 = \frac{Dose1/Range1}{(Dose1/Range1 + Dose2/Range2 + Dose3/Range3)} \times Agent1\ Effect$$

$$FOE2 = \frac{Dose2/Range2}{(Dose1/Range1 + Dose2/Range2 + Dose3/Range3)} \times Agent2\ Effect$$

$$FOE3 = \frac{Dose3/Range3}{(Dose1/Range1 + Dose2/Range2 + Dose3/Range3)} \times Agent3\ Effect$$

Multi-agent (n Agents) Therapy

The concept underlying this multi-agent dosing model is that each agent has some contribution to the overall effect. This contribution is determined by the amount of each agent the patient is using as well as the intrinsic potency of each agent. The overall proportion of each agent is determined by the amount of agent as it relates to the dosing range. The overall proportion as well as the intrinsic potency of the agent is used to determine the total proportional effect which each agent has on the surrogate marker. This parameter (FOE1, FOE2 . . . FOEn) is then inserted into the four-parameter equation (NAD1, NAD2 . . . NADn) for calculating dose by adjusting the proportional change in marker that is attributed to the activity of the agent.

To Calculate the Range for the First Agent $NAD1=CAD1+(\%\ change\ level\ First/MF)/1+(CAD1/DrugRange1))*CAD1$ To Calculate the Dose for the Second Agent $NAD2=CAD2+(\%\ change\ level\ Second/MF)/1+(CAD2/DrugRange2))*CAD2$ To Calculate the Dose for the nth Agent $NADn=CADn+(\%\ change\ level\ nth/MF)/1+(CADn/DrugRangen))*CADn$ where:

% change level First=(DDNM−CDNM)*FOE1/CDNM For regular markers
% change level First=(CDNM−DDNM)*FOE1/CDNM For inverse markers
% change level Second=(DDNM−CDNM)*FOE2/CDNM For regular markers
% change level Second=(CDNM−DDNM)*FOE2/CDNM For inverse markers
% change level nth=(DDNM−CDNM)*FOEn/CDNM For regular markers
% change level nth=(CDNM−DDNM)*FOEn/CDNM For inverse markers
CAD1=Current agent dose of the first agent
CAD2=Current agent dose of the second agent
CADn=Current agent dose of the nth agent
NAD1 high First=New first agent high dose range value
NAD2 high Second=New second agent high dose range value
NADn high Third=New nth agent high dose range value
CDNM1=Current agent numerical marker for the first agent
CDNM2=Current agent numerical marker for the second agent
CDNMn=Current agent numerical marker for the nth agent
DDNM1=Desired agent numerical marker for the first agent
DDNM2=Desired agent numerical marker for the second agent
DDNMn=Desired agent numerical marker for the nth agent
FOE1=Factor of effect the first agent has on its associated numerical marker
FOE2=Factor of effect the second agent has on its associated numerical marker
FOEn=Factor of effect the nth agent has on its associated numerical marker To Calculate the Level/Response for the First Agent $NDL1=-1*CDL*((NDD1*MF*DrugRange1+ NDD1*MF*CDD1*MF*DrugRange1-1*CDD1\hat{}2*MF-1*DrugRange1*CDD1)/(DrugRange1*CDD1))$ To Calculate the Level/Response for the Second Agent $NDL2=-1*NDL1*((NDD2*MF*DrugRange2+ NDD2*MF*CDD2*MF*DrugRange2-1*CDD2\hat{}2*MF-1*DrugRange2*CDD2)/(DrugRange2*CDD2))$ To Calculate the Level/Response for the Third Agent $NDLn=-1*NDLn1*((NDDn*MF*DrugRangen+ NDDn*MFn*CDDn*MFn*DrugRangen-1*CDDn\hat{}2*MFn-1*DrugRangen*CDDn)/(DrugRangen*CDDn))$ Wherein,
NDL1=New First Drug Level
NDL2=New Second Drug Level
NDL3=New Third Drug Level
CDL=Current Drug Level
MarkerFunction1 (MF1)=1.5^ (CDL/MarkerRange)
MarkerRange=The maximal range typically seen for marker.
DrugRange1=The maximal range typically prescribed for the drug1.
DrugRange2=The maximal range typically prescribed for the drug2.
DrugRange3=The maximal range typically prescribed for the drug3.

To Calculate the Proportion of Effect Based on the Amount of Agent and the Agent's Intrinsic Effect Agent1 Effect=1
Agent2 Effect=1
Agent n Effect=1

$$Agent1\ Proportion = \frac{Dose1/Range1}{(Dose1/Range1 + Dose2/Range2 + \ldots Dose\ n/Range\ n)}$$

$$Agent2\ Proportion = \frac{Dose2/Range2}{(Dose1/Range1 + Dose2/Range2 + \ldots Dose\ n/Range\ n)}$$

$$Agent\ n\ Proportion = \frac{Dose\ n/Range\ n}{(Dose1/Range1 + Dose2/Range2 + \ldots Dose\ n/Range\ n)}$$

$$FOE1 = \underbrace{\frac{Dose1/Range1}{(Dose1/Range1 + Dose2/Range2 + \ldots Dose\ n/Range\ n)} \times}_{Agent1\ Effect}$$

$$FOE2 = \underbrace{\frac{Dose2/Range2}{(Dose1/Range1 + Dose2/Range2 + \ldots Dose\ n/Range\ n)} \times}_{Agent2\ Effect}$$

$$FOEn = \underbrace{\frac{(Dose\ n/Range\ n)}{(Dose1/Range1 + Dose2/Range2 + \ldots Dose\ n/Range\ n)} \times}_{Agent\ n\ Effect}$$

Although the invention has been described in detail in the foregoing for the purpose of illustration, it is to be understood that such detail is solely for that purpose and that variations can be made therein by those of ordinary skill in the art without departing from the spirit and scope of the invention as defined by the following claims, including all equivalents thereof.

What is claimed is:

1. A method for calculating a next dose for each agent of an agent therapy accounting for the level or degree of response that a patient has to each agent, comprising the steps of:

accepting as first inputs the patient's current dose of an agent which the patient may be using;

accepting as second inputs at least one numerical marker indicating at least one response of the patient; and calculating a new agent dose for said agent as a function of said first inputs, said second inputs, and a contribution that each agent makes to an overall effect to be achieved by said multi-agent therapy, wherein said calculating is performed as follows:

To Calculate the Dose for One Agent $NDD=CDD+((\%\ \text{change level}/MF))/1+(CDD/DrugRange))*CDD$ wherein, % change level=(DDNM−CDNM)/CDNM For regular markers % change level=(CDNM−DDNM)/CDNM For inverse markers NDD=New Drug Dose CDD=Current Drug Dose CDNM=Current Drug Numerical Marker DDNM=Desired Drug Numerical Marker MarkerFunction (MF)=1.5^ (CDNM/MarkerRange)

MarkerRange=The maximal range typically seen for the marker

DrugRange=The maximal range typically prescribed for the drug

To Calculate the Level/Response for One Agent $NDL=-1*CDL*((NDD*MF*DrugRange+NDD*MF*CDD*MF*DrugRange-1*CDD\hat{\ }2*MF-1*DrugRange*CDD)/(DrugRange*CDD))$ wherein, NDL=New Drug Level NDD=New Drug Dose CDL=Current Drug Level CDD=Current Drug Dose MarkerFunction (MD=1.5^ (CDNM/MarkerRange)

MarkerRange=The maximal range typically seen for the marker

DrugRange=The maximal range typically prescribed for the drug.

2. A method of calculating the best next dose for each agent of a multi-agent therapy which a patient may be using and accounting for the level or degree of response that a patient has to each agent, comprising the steps of:

accepting as first inputs the patient's current doses of a plurality of agents which the patient may be using;

accepting as second inputs one or more numerical markers indicating one or more responses of the patient; and calculating new agent doses for said agent or plurality of agents as a function of said first inputs, said second inputs, and contributions which each agent makes to an overall effect to be achieved by said multi-agent therapy, wherein said calculating is performed as follows:

To Calculate the Dose for the First Agent $NAD1=CAD1+(\%\ \text{change level First}/MF)/1+(CAD1/DrugRange1))*CAD1$ To Calculate the Dose for the Second Agent $NAD2=CAD2+(\%\ \text{change level Second}/MF)/1+(CAD2/DrugRange2))*CAD2$ wherein, % change level First=(DDNM−CDNM)*FOE1/CDNM For regular markers % change level First=(CDNM−DDNM)*FOE1/CDNM For inverse markers % change level Second=(DDNM−CDNM)*FOE2/CDNM For regular markers % change level Second=(CDNM−DDNM)*FOE2/CDNM For inverse markers CAD1=Current agent dose of the first agent CAD2=Current agent dose of the second agent NAD1=New first agent dose value NAD2=New second agent dose value CDNM1=Current agent numerical marker for the first agent CDNM2=Current agent numerical marker for the second agent DDNM1=Desired agent numerical marker for the first agent DDNM2=Desired agent numerical marker for the second agent FOE1=Factor of effect the first agent has on its associated numerical marker FOE2=Factor of effect the second agent has on its associated numerical marker MarkerFunction (MF)=1.5^ (CDNM/MarkerRange)

MarkerRange=The maximal range typically seen for the marker

DrugRange1=The maximal range typically prescribed for drug1

DrugRange2=The maximal range typically prescribed for drug2

To Calculate the Level/Response for the First Agent $$NDL1=-1*CDL*((NDD1*MF*DrugRange1 NDD1*MF*CDD1*MF*DrugRange1-1*CDD1\hat{}2*MF-1*DrugRange1*CDD1)/(DrugRange1*CDD1))$$

To Calculate the Level/Response for the Second Agent $$NDL2=-1*NDL1*((NDD2*MF*DrugRange2+NDD2*MF*CDD2*MF*DrugRange2-1*CDD2\hat{}2*MF-1*DrugRange2*CDD2)/(DrugRange2*CDD2))$$

wherein,

NDL1=New First Drug Level

NDL2=New Second Drug Level

CDL=Current Drug Level

MarkerFunction1 (MF1)=1.5 ^ (CDL/MarkerRange)

MarkerFunction2 (MF2)=1.5 ^ (CDL/MarkerRange)

MarkerRange=The maximal range typically seen for marker

DrugRange1=The maximal range typically prescribed for the drug1

DrugRange2=The maximal range typically prescribed for the drug2

To Calculate the Proportion of Effect Based on the Amount of Agent and the Agent's Intrinsic Effect Agent1 Effect=1

Agent2 Effect=1

$$Agent1\ Proportion = \frac{Dose1/Range1}{(Dose1/Range1 + Dose2/Range2)}$$

$$Agent2\ Proportion = \frac{Dose2/Range2}{(Dose1/Range1 + Dose2/Range2)}$$

$$FOE1 = \frac{Dose1/Range1}{(Dose1/Range1 + Dose2/Range2)} \times Agent1\ Effect$$

$$FOE2 = \frac{Dose2/Range2}{(Dose1/Range1 + Dose2/Range2)} \times Agent2\ Effect.$$

3. A method of calculating the best next dose for each agent of a multi-agent therapy which a patient may be using and accounting for the level or degree of response that a patient has to each agent, comprising the steps of:

accepting as first inputs the patient's current doses of a plurality of agents which the patient may be using;

accepting as second inputs one or more numerical markers indicating one or more responses of the patient; and calculating new agent doses for said agent or plurality of agents as a function of said first inputs, said second inputs, and contributions which each agent makes to an overall effect to be achieved by said multi-agent therapy, wherein said calculating is performed as follows:

To Calculate the Dose for the First Agent $$NAD1=CAD1+(\%\ \text{change level First}/MF)/1+(CAD1/DrugRange1))*CAD1$$

To Calculate the Dose for the Second Agent $$NAD2=CAD2+(\%\ \text{change level Second}/MF)/1+(CAD2/DrugRange2))*CAD2$$

To Calculate the Dose for the Third Agent $$NAD3=CAD3+(\%\ \text{change level Third}/MF)/1 +(CAD3/DrugRange3))*CAD3$$

where:

% change level First=(DDNM−CDNM)*FOE1/CDNM For regular markers

% change level First=(CDNM−DDNM)*FOE1/CDNM For inverse markers

% change level Second=(DDNM−CDNM)*FOE2/CDNM For regular markers

% change level Second=(CDNM−DDNM)*FOE2/CDNM For inverse markers

% change level Third=(DDNM−CDNM)*FOE3/CDNM For regular markers

% change level Third=(CDNM−DDNM)*FOE3/CDNM For inverse markers

CAD1=Current agent dose of the first agent

CAD2=Current agent dose of the second agent

CAD3=Current agent dose of the third agent

NAD1 high First=New first agent high dose range value

NAD2 high Second=New second agent high dose range value

NAD3 high Third=New third agent high dose range value

CDNM1=Current agent numerical marker for the first agent

CDNM2=Current agent numerical marker for the second agent

CDNM3=Current agent numerical marker for the third agent

DDNM1=Desired agent numerical marker for the first agent

DDNM2=Desired agent numerical marker for the second agent

DDNM3=Desired agent numerical marker for the third agent

FOE1=Factor of effect the first agent has on its associated numerical marker

FOE2=Factor of effect the second agent has on its associated numerical marker

FOE3=Factor of effect the third agent has on its associated numerical marker

To Calculate the Level/Response for the First Agent $$NDL1=-1*CDL*((NDD1*MF*DrugRange1+NDD1*MF*CDD1*MF*DrugRange1-1*CDD1\hat{}2*MF-1*DrugRange1*CDD1)/(DrugRange1*CDD1))$$

To Calculate the Level/Response for the Second Agent $$NDL2=-1*NDL1*((NDD2*MF*DrugRange2+\\ NDD2*MF*CDD2*MF*DrugRange2-1*CDD2\textasciicircum 2*MF-\\ 1*DrugRange2*CDD2)/(DrugRange2*CDD2))$$

To Calculate the Level/Response for the Third Agent $$NDL3=-1*NDL2*((NDD3*MF*DrugRange3+\\ NDD3*MF*CDD3*MF*DrugRange3-1*CDD3\textasciicircum 2*MF-\\ 1*DrugRange3*CDD3)/(DrugRange3*CDD3))$$

wherein,
 NDL1=New First Drug Level
 NDL2=New Second Drug Level
 NDL3=New Third Drug Level
 CDL=Current Drug Level
 MarkerFunction1 (MF1)=1.5 ^ (CDL/MarkerRange)
 MarkerRange=The maximal range typically seen for marker
 DrugRange1=The maximal range typically prescribed for the drug1
 DrugRange2=The maximal range typically prescribed for the drug2
 DrugRange3=The maximal range typically prescribed for the drug3

To Calculate the Proportion of Effect Based on the Amount of Agent and the Agent's Intrinsic Effect
 Agent1 Effect=1
 Agent2 Effect=1
 Agent3 Effect=1

$$Agent1\ Proportion = \frac{Dose1/Range1}{(Dose1/Range1+Dose2/Range2+Dose3/Range3)}$$

$$Agent2\ Proportion = \frac{Dose2/Range2}{(Dose1/Range1+Dose2/Range2+Dose3/Range3)}$$

$$Agent3\ Proportion = \frac{Dose3/Range3}{(Dose1/Range1+Dose2/Range2+Dose3/Range3)}$$

$$FOE1 = \frac{Dose1/Range1}{(Dose1/Range1+Dose2/Range2+Dose3/Range3)} \times Agent1\ Effect$$

$$FOE2 = \frac{Dose2/Range2}{(Dose1/Range1+Dose2/Range2+Dose3/Range3)} \times Agent2\ Effect$$

$$FOE3 = \frac{Dose3/Range3}{(Dose1/Range1+Dose2/Range2+Dose3/Range3)} \times Agent3\ Effect.$$

4. A method of calculating the best next dose for each agent of a multi-agent therapy which a patient may be using and accounting for the level or degree of response that a patient has to each agent, comprising the steps of:
 accepting as first inputs the patient's current doses of a plurality of agents which the patient may be using;
 accepting as second inputs one or more numerical markers indicating one or more responses of the patient; and
 calculating new agent doses for said agent or plurality of agents as a function of said first inputs, said second inputs, and contributions which each agent makes to an overall effect to be achieved by said multi-agent therapy, wherein said calculating is performed as follows:

To Calculate the Range for the First Agent $$NAD1=CAD1+(\%\ \text{change level First}/MF)/1+(CAD1/\\ DrugRange1))*CAD1$$

To Calculate the Dose for the Second Agent $$NAD2=CAD2+(\%\ \text{change level Second}/MF)/1+(CAD2/\\ DrugRange2))*CAD2$$

To Calculate the Dose for the nth Agent $$NADn=CADn+(\%\ \text{change level}\ nth/MF)/1+(CADn/\\ DrugRangen))*CADn$$

wherein,
 % change level First=(DDNM−CDNM)*FOE1/CDNM For regular markers
 % change level First=(CDNM−DDNM)*FOE1/CDNM For inverse markers
 % change level Second=(DDNM−CDNM)*FOE2/CDNM For regular markers
 % change level Second=(CDNM−DDNM)*FOE2/CDNM For inverse markers
 % change level nth=(DDNM−CDNM)*FOEn/CDNM For regular markers
 % change level nth=(CDNM−DDNM)*FOEn/CDNM For inverse markers
 CAD1=Current agent dose of the first agent
 CAD2=Current agent dose of the second agent
 CADn=Current agent dose of the nth agent
 NAD1 high First=New first agent high dose range value
 NAD2 high Second=New second agent high dose range value
 NADn high Third=New nth agent high dose range value
 CDNM1=Current agent numerical marker for the first agent
 CDNM2=Current agent numerical marker for the second agent
 CDNMn=Current agent numerical marker for the nth agent
 DDNM1=Desired agent numerical marker for the first agent
 DDNM2=Desired agent numerical marker for the second agent
 DDNMn=Desired agent numerical marker for the nth agent
 FOE1=Factor of effect the first agent has on its associated numerical marker
 FOE2=Factor of effect the second agent has on its associated numerical marker
 FOEn=Factor of effect the nth agent has on its associated numerical marker To Calculate the Level/Response for the First Agent $$NDL1=-1*CDL*((NDD1*MF*DrugRange1+\\ NDD1*MF*CDD1*MF*DrugRange1-1*CDD1\textasciicircum 2*MF-\\ 1*DrugRange1*CDD1)/(DrugRange1*CDD1))$$

To Calculate the Level/Response for the Second Agent $$NDL2=-1*NDL1*((NDD2*MF*DrugRange2+\\ NDD2*MF*CDD2*MF*DrugRange2-1*CDD2\textasciicircum 2*MF-\\ 1*DrugRange2*CDD2)/(DrugRange2*CDD2))$$

To Calculate the Level/Response for the Third Agent $$NDLn=-1*NDLn1*((NDDn*MF*DrugRangen+\\NDDn*MFn*CDDn*MFn\ DrugRangen-1*CDDn2\hat{}2*MFn-\\1*DrugRangen*CDDn)/(DrugRangen*CDDn))$$

wherein,
NDL1=New First Drug Level
NDL2=New Second Drug Level
NDL3=New Third Drug Level
CDL=Current Drug Level
MarkerFunction1 (MF1)=1.5 ^ (CDL/MarkerRange)
MarkerRange=The maximal range typically seen for marker.
DrugRange1=The maximal range typically prescribed for the drug1
DrugRange2=The maximal range typically prescribed for the drug2
DrugRange3=The maximal range typically prescribed for the drug3

To Calculate the Proportion of Effect Based on the Amount of Agent and the Agent's Intrinsic Effect
Agent1 Effect=1
Agent2 Effect=1
Agent n Effect=1

$Agent1\ Proportion =$ $$\frac{Dose1/Range1}{(Dose1/Range1+Dose2/Range2+\ldots\ Dose\ n/Range\ n)}$$

$Agent2\ Proportion =$ $$\frac{Dose2/Range2}{(Dose1/Range1+Dose2/Range2+\ldots\ Dose\ n/Range\ n)}$$

$Agent\ n\ Proportion =$ $$\frac{Dose\ n/Range\ n}{(Dose1/Range1+Dose2/Range2+\ldots\ Dose\ n/Range\ n)}$$

$FOE1 =$ $$\frac{Dose1/Range1}{(Dose1/Range1+Dose2/Range2+\ldots\ Dose\ n/Range\ n)} \times$$

$Agent1\ Effect$ $FOE2 =$ $$\frac{Dose2/Range2}{(Dose1/Range1+Dose2/Range2+\ldots\ Dose\ n/Range\ n)} \times$$

$Agent2\ Effect$ $FOEn =$ $$\frac{(Dose\ n/Range\ n)}{(Dose1/Range1+Dose2/Range2+\ldots\ Dose\ n/Range\ n)} \times$$

$Agent\ n\ Effect.$

5. A storage device having stored thereon an ordered set of instructions which, when executed by a computer, performs a predetermined method, comprising:
first means for accepting as first inputs a patient's current doses of a plurality of agents which the patient may be using;
second means for accepting as second inputs one or more numerical markers indicating one or more responses of the patient; and
third means for calculating new agent doses for said plurality of agents as a function of said first inputs, said second inputs, accounting for the level or degree of response that a patient has to each agent, and contributions which each agent makes to an overall effect to be achieved by said multi-agent therapy, wherein said means calculates said new agent doses as follows:

To Calculate the Dose for the First Agent $$NAD1=CAD1+(\%\ change\ level\ First/MF)/1+(CAD1/\\DrugRange1))*CAD1$$

To Calculate the Dose for the Second Agent $$NAD2=CAD2+(\%\ change\ level\ Second/MF)/1+(CAD2/\\DrugRange2))*CAD2$$

wherein,
% change level First=(DDNM−CDNM)*FOE1/CDNM For regular markers
% change level First=(CDNM−DDNM)*FOE1/CDNM For inverse markers
% change level Second=(DDNM−CDNM)*FOE2/CDNM For regular markers
% change level Second=(CDNM−DDNM)*FOE2/CDNM For inverse markers
CAD1=Current agent dose of the first agent
CAD2=Current agent dose of the second agent
NAD1=New first agent dose value
NAD2=New second agent dose value
CDNM1=Current agent numerical marker for the first agent
CDNM2=Current agent numerical marker for the second agent
DDNM1=Desired agent numerical marker for the first agent
DDNM2=Desired agent numerical marker for the second agent
FOE1=Factor of effect the first agent has on its associated numerical marker
FOE2=Factor of effect the second agent has on its associated numerical marker
MarkerFunction (MF)=1.5 ^ (CDNM/MarkerRange)
MarkerRange=The maximal range typically seen for the marker
DrugRange1=The maximal range typically prescribed for drug1
DrugRange2=The maximal range typically prescribed for drug2

To Calculate the Level/Response for the First Agent $$NDL1=-1*CDL*((NDD1*MF*DrugRange1+\\NDD1*MF*CDD1*MF*DrugRange1-1*CDD1\hat{}2*MF-\\1*DrugRange1*CDD1)/(DrugRange1*CDD1))$$

To Calculate the Level/Response for the Second Agent $$NDL2=-1*NDL1*((NDD2*MF*DrugRange2+\\NDD2*MF*CDD2*MF*DrugRange2-1*CDD2\hat{}2*MF-\\1*DrugRange2*CDD2)/(DrugRange2*CDD2))$$

wherein,
NDL1=New First Drug Level
NDL2=New Second Drug Level
CDL=Current Drug Level
MarkerFunction1 (MF1)=1.5 ^ (CDL/MarkerRange)
MarkerFunction2 (MF2)=1.5 ^ (CDL/MarkerRange)
MarkerRange=The maximal range typically seen for marker DrugRange1=The maximal range typically prescribed for the drug1

DrugRange2=The maximal range typically prescribed for the drug2

To Calculate the Proportion of Effect Based on the Amount of Agent and the Agent's Intrinsic Effect Agent1 Effect=1

Agent2 Effect=1

$$Agent1\ Proportion = \frac{Dose1/Range1}{(Dose1/Range1 + Dose2/Range2)}$$

$$Agent2\ Proportion = \frac{Dose2/Range2}{(Dose1/Range1 + Dose2/Range2)}$$

$$FOE1 = \frac{Dose1/Range1}{(Dose1/Range1 + Dose2/Range2)} \times Agent1\ Effect$$

$$FOE2 = \frac{Dose2/Range2}{(Dose1/Range1 + Dose2/Range2)} \times Agent2\ Effect.$$

6. A storage device having stored thereon an ordered set of instructions which, when executed by a computer, performs a predetermined method, comprising:

first means for accepting as first inputs a patient's current doses of a plurality of agents which the patient may be using;

second means for accepting as second inputs one or more numerical markers indicating one or more responses of the patient; and third means for calculating new agent doses for said plurality of agents as a function of said first inputs, said second inputs, accounting for the level or degree of response that a patient has to each agent, and contributions which each agent makes to an overall effect to be achieved by said multi-agent therapy, wherein said means calculates said new agent doses as follows:

To Calculate the Dose for the First Agent $NAD1=CAD1+(\%$ change level First$/MF)/1+(CAD1/$DrugRange1$))*CAD1$ To Calculate the Dose for the Second Agent $NAD2=CAD2+(\%$ change level Second$/MF)/1+(CAD2/$DrugRange2$))*CAD2$ To Calculate the Dose for the Third Agent $NAD3=CAD3+(\%$ change level Third$/MF)/1+(CAD3/$DrugRange3$))*CAD3$ where:

% change level First=(DDNM−CDNM)*FOE1/CDNM For regular markers

% change level First=(CDNM−DDNM)*FOE1/CDNM For inverse markers

% change level Second=(DDNM−CDNM)*FOE2/CDNM For regular markers

% change level Second=(CDNM−DDNM)*FOE2/CDNM For inverse markers

% change level Third=(DDNM−CDNM)*FOE3/CDNM For regular markers

% change level Third=(CDNM−DDNM)*FOE3/CDNM For inverse markers

CAD1=Current agent dose of the first agent

CAD2=Current agent dose of the second agent

CAD3=Current agent dose of the third agent

NAD1 high First=New first agent high dose range value

NAD2 high Second=New second agent high dose range value

NAD3 high Third=New third agent high dose range value

CDNM1=Current agent numerical marker for the first agent

CDNM2=Current agent numerical marker for the second agent

CDNM3=Current agent numerical marker for the third agent

DDNM1=Desired agent numerical marker for the first agent

DDNM2=Desired agent numerical marker for the second agent

DDNM3=Desired agent numerical marker for the third agent

FOE1=Factor of effect the first agent has on its associated numerical marker

FOE2=Factor of effect the second agent has on its associated numerical marker

FOE3=Factor of effect the third agent has on its associated numerical marker

To Calculate the Level/Response for the First Agent $NDL1=-1*CDL*((NDD1*MF*DrugRange1+ NDD1*MF*CDD1*MF*DrugRange1-1*CDD1\hat{\ }2*MF- 1*DrugRange1*CDD1)/(DrugRange1*CDD1))$ To Calculate the Level/Response for the Second Agent $NDL2=-1*NDL1*((NDD2*MF*DrugRange2+ NDD2*MF*CDD2*MF*DrugRange2-1*CDD2\hat{\ }2*MF- 1*DrugRange2*CDD2)/(DrugRange2*CDD2))$ To Calculate the Level/Response for the Third Agent $NDL3=-1*NDL2*((NDD3*MF*DrugRange3+ NDD3*MF*CDD3*MF*DrugRange3-1*CDD3\hat{\ }2*MF- 1*DrugRange3*CDD3)/(DrugRange3*CDD3))$ wherein, NDL1=New First Drug Level NDL2=New Second Drug Level NDL3=New Third Drug Level CDL=Current Drug Level MarkerFunction1 (MF1)=1.5 ^ (CDL/MarkerRange)

MarkerRange=The maximal range typically seen for marker

DrugRange1=The maximal range typically prescribed for the drug1

DrugRange2=The maximal range typically prescribed for the drug2

DrugRange3=The maximal range typically prescribed for the drug3

To Calculate the Proportion of Effect Based on the Amount of Agent and the Agent's Intrinsic Effect Agent1 Effect=1
Agent2 Effect=1
Agent3 Effect=1

$$Agent1\ Proportion = \frac{Dose1/Range1}{(Dose1/Range1 + Dose2/Range2 + Dose3/Range3)}$$

$$Agent2\ Proportion = \frac{Dose2/Range2}{(Dose1/Range1 + Dose2/Range2 + Dose3/Range3)}$$

$$Agent3\ Proportion = \frac{Dose3/Range3}{(Dose1/Range1 + Dose2/Range2 + Dose3/Range3)}$$

$$FOE1 = \frac{Dose1/Range1}{(Dose1/Range1 + Dose2/Range2 + Dose3/Range3)} \times Agent1\ Effect$$

$$FOE2 = \frac{Dose2/Range2}{(Dose1/Range1 + Dose2/Range2 + Dose3/Range3)} \times Agent2\ Effect$$

$$FOE3 = \frac{Dose3/Range3}{(Dose1/Range1 + Dose2/Range2 + Dose3/Range3)} \times Agent3\ Effect.$$

7. A storage device having stored thereon an ordered set of instructions which, when executed by a computer, performs a predetermined method, comprising:

first means for accepting as first inputs a patient's current doses for n number of agents which the patient may be using;

second means for accepting as second inputs one or more numerical markers indicating one or more responses of the patient; and third means for calculating new agent doses for said n number of agents as a function of said first inputs, said second inputs, accounting for the level or degree of response that a patient has to each agent, and contributions which each agent makes to an overall effect to be achieved by said multi-agent therapy, wherein said means calculates said new agent doses as follows:

To Calculate the Range for the First Agent $NAD1=CAD1+(\%$ change level First$/MF)/1+(CAD1/$DrugRange1$))*CAD1$ To Calculate the Dose for the Second Agent $NAD2=CAD2 +(\%$ change level Second$/MF)/1+(CAD2/$DrugRange2$))*CAD2$ To Calculate the Dose for the nth Agent $NADn=CADn+(\%$ change level $nth/MF)/1+(CADn/$DrugRangen$))*CADn$ wherein, % change level First=(DDNM−CDNM)*FOE1/CDNM For regular markers % change level First=(CDNM−DDNM)*FOE1/CDNM For inverse markers % change level Second=(DDNM−CDNM)*FOE2/CDNM For regular markers % change level Second=(CDNM−DDNM)*FOE2/CDNM For inverse markers % change level nth=(DDNM−CDNM)*FOEn/CDNM For regular markers % change level nth=(CDNM−DDNM)*FOEn/CDNM For inverse markers CAD1=Current agent dose of the first agent
CAD2=Current agent dose of the second agent
CADn=Current agent dose of the nth agent
NAD1 high First=New first agent high dose range value
NAD2 high Second=New second agent high dose range value
NADn high Third=New nth agent high dose range value
CDNM1=Current agent numerical marker for the first agent
CDNM2=Current agent numerical marker for the second agent
CDNMn=Current agent numerical marker for the nth agent
DDNM1=Desired agent numerical marker for the first agent
DDNM2=Desired agent numerical marker for the second agent
DDNMn=Desired agent numerical marker for the nth agent
FOE1=Factor of effect the first agent has on its associated numerical marker
FOE2=Factor of effect the second agent has on its associated numerical marker
FOEn=Factor of effect the nth agent has on its associated numerical marker To Calculate the Level/Response for the First Agent $NDL1=-1*CDL*((NDD1*MF*DrugRange1+NDD1*MF*CDD1*MF*DrugRange1-1*CDD1^2*MF-1*DrugRange1*CDD1)/(DrugRange1*CDD1))$ To Calculate the Level/Response for the Second Agent $NDL2=-1*NDL1*((NDD2*MF*DrugRange2+NDD2*MF*CDD2*MF*DrugRange2-1*CDD2^2*MF-1*DrugRange2*CDD2)/(DrugRange2*CDD2))$ To Calculate the Level/Response for the Third Agent $NDLn=-1*NDLn-1*((NDDn*MF*DrugRangen+NDDn*MFn*CDDn*MFn*DrugRangen-1*CDDn2^2*MFn-1*DrugRangen*CDDn)/(DrugRangen*CDDn))$ wherein, NDL1=New First Drug Level
NDL2=New Second Drug Level
NDL3=New Third Drug Level
CDL=Current Drug Level
MarkerFunction1 (MF1)=1.5 ^ (CDL/MarkerRange)
MarkerRange=The maximal range typically seen for marker.
DrugRange1=The maximal range typically prescribed for the drug1
DrugRange2=The maximal range typically prescribed for the drug2
DrugRange3=The maximal range typically prescribed for the drug3

To Calculate the Proportion of Effect Based on the Amount of Agent and the Agent's Intrinsic Effect Agent1 Effect=1
Agent2 Effect=1
Agent n Effect=1

$$Agent1\ Proportion = \frac{Dose1/Range1}{(Dose1/Range1 + Dose2/Range2 + \ldots\ Dose\ n/Range\ n)}$$

$$Agent2\ Proportion = \frac{Dose2/Range2}{(Dose1/Range1 + Dose2/Range2 + \ldots\ Dose\ n/Range\ n)}$$

$$Agent\ n\ Proportion = \frac{Dose\ n/Range\ n}{(Dose1/Range1 + Dose2/Range2 + \ldots\ Dose\ n/Range\ n)}$$

$$FOE1 = \frac{Dose1/Range1}{(Dose1/Range1 + Dose2/Range2 + \ldots\ Dose\ n/Range\ n)} \times Agent1\ Effect$$

$$FOE2 = \frac{Dose2/Range2}{(Dose1/Range1 + Dose2/Range2 + \ldots\ Dose\ n/Range\ n)} \times Agent2\ Effect$$

$$FOEn = \frac{(Dose\ n/Range\ n)}{(Dose1/Range1 + Dose2/Range2 + \ldots\ Dose\ n/Range\ n)} \times Agent\ n\ Effect.$$

8. An apparatus for calculating the next best dose for each agent of a multi-agent therapy which a patient may be using and accounting for the level or degree of response that a patient has to each agent, comprising:

first means for accepting as first inputs the patient's current doses of a plurality of agents which the patient may be using;

second means for accepting as second inputs one or more numerical markers indicating one or more responses of the patient; and third means for calculating new agent doses for said plurality of agents as a function of said first inputs, said second inputs, and contributions which each agent makes to an overall effect to be achieved by said multi-agent therapy, wherein said third means calculates said new agent doses as follows:

To Calculate the Dose for the First Agent $NAD1=CAD1+(\%\ change\ level\ First/MF)/1+(CAD1/DrugRange1))*CAD1$ To Calculate the Dose for the Second Agent $NAD2=CAD2+(\%\ change\ level\ Second/MF)/1+(CAD2/DrugRange2))*CAD2$ wherein, % change level First=(DDNM−CDNM)*FOE1/CDNM For regular markers % change level First=(CDNM−DDNM)*FOE1/CDNM For inverse markers % change level Second=(DDNM−CDNM)*FOE2/CDNM For regular markers % change level Second=(CDNM−DDNM)*FOE2/CDNM For inverse markers CAD1=Current agent dose of the first agent
CAD2=Current agent dose of the second agent
NAD1=New first agent dose value
NAD2=New second agent dose value
CDNM1=Current agent numerical marker for the first agent
CDNM2=Current agent numerical marker for the second agent
DDNM1=Desired agent numerical marker for the first agent
DDNM2=Desired agent numerical marker for the second agent
FOE1=Factor of effect the first agent has on its associated numerical marker
FOE2=Factor of effect the second agent has on its associated numerical marker
MarkerFunction (MF)=1.5 ^ (CDNM/MarkerRange)
MarkerRange=The maximal range typically seen for the marker
DrugRange1=The maximal range typically prescribed for drug1
DrugRange2=The maximal range typically prescribed for drug2

To Calculate the Level/Response for the First Agent $NDL1=-1*CDL*((NDD1*MF*DrugRange1+$
$NDD1*MF*CDD1*MF*DrugRange1-1*CDD1\hat{}2*MF-$
$1*DrugRange1*CDD1)/(DrugRange1*CDD1))$ To Calculate the Level/Response for the Second Agent $NDL2=-1*NDL1*((NDD2*MF*DrugRange2+$
$NDD2*MF*CDD2*MF*DrugRange2-1*CDD2\hat{}2*MF-$
$1*DrugRange2*CDD2)/(DrugRange2*CDD2))$ wherein, NDL1=New First Drug Level
NDL2=New Second Drug Level
CDL=Current Drug Level
MarkerFunction1 (MF1)=1.5 ^ (CDL/MarkerRange)
MarkerFunction2 (MF2)=1.5 ^ (CDL/MarkerRange)
MarkerRange=The maximal range typically seen for marker
DrugRange1=The maximal range typically prescribed for the drug1
DrugRange2=The maximal range typically prescribed for the drug2

To Calculate the Proportion of Effect Based on the Amount of Agent and the Agent's Intrinsic Effect Agent1 Effect=1
Agent2 Effect=1

$$Agent1\ Proportion = \frac{Dose1/Range1}{(Dose1/Range1 + Dose2/Range2)}$$

$$Agent2\ Proportion = \frac{Dose2/Range2}{(Dose1/Range1 + Dose2/Range2)}$$

$$FOE1 = \frac{Dose1/Range1}{(Dose1/Range1 + Dose2/Range2)} \times Agent1\ Effect$$

$$FOE2 = \frac{Dose2/Range2}{(Dose1/Range1 + Dose2/Range2)} \times Agent2\ Effect.$$

9. An apparatus for calculating the next best dose for each agent of a multi-agent therapy which a patient may be using and accounting for the level or degree of response that a patient has to each agent, comprising:
- first means for accepting as first inputs the patient's current doses of a plurality of agents which the patient may be using;
- second means for accepting as second inputs one or more numerical markers indicating one or more responses of the patient; and
- third means for calculating new agent doses for said plurality of agents as a function of said first inputs, said second inputs, and contributions which each agent makes to an overall effect to be achieved by said multi-agent therapy, wherein said third means calculates said new agent doses as follows To Calculate the Dose for the First Agent $$NAD1=CAD1+(\% \text{ change level First}/MF)/1+(CAD1/DrugRange1))*CAD1$$

To Calculate the Dose for the Second Agent $$NAD2=CAD2+(\% \text{ change level Second}/MF)/1+(CAD2/DrugRange2))*CAD2$$

To Calculate the Dose for the Third Agent $$NAD3=CAD3+(\% \text{ change level Third}/MF)/1+(CAD3/DrugRange3))*CAD3$$

where:
- % change level First=(DDNM−CDNM)*FOE1/CDNM For regular markers
- % change level First=(CDNM−DDNM)*FOE1/CDNM For inverse markers
- % change level Second=(DDNM−CDNM)*FOE2/CDNM For regular markers
- % change level Second=(CDNM−DDNM)*FOE2/CDNM For inverse markers
- % change level Third=(DDNM−CDNM)*FOE3/CDNM For regular markers
- % change level Third=(CDNM−DDNM)*FOE3/CDNM For inverse markers
- CAD1=Current agent dose of the first agent
- CAD2=Current agent dose of the second agent
- CAD3=Current agent dose of the third agent
- NAD1 high First=New first agent high dose range value
- NAD2 high Second=New second agent high dose range value
- NAD3 high Third=New third agent high dose range value
- CDNM1=Current agent numerical marker for the first agent
- CDNM2=Current agent numerical marker for the second agent
- CDNM3=Current agent numerical marker for the third agent
- DDNM1=Desired agent numerical marker for the first agent
- DDNM2=Desired agent numerical marker for the second agent
- DDNM3=Desired agent numerical marker for the third agent
- FOE1=Factor of effect the first agent has on its associated numerical marker
- FOE2=Factor of effect the second agent has on its associated numerical marker
- FOE3=Factor of effect the third agent has on its associated numerical marker To Calculate the Level/Response for the First Agent $$NDL1=-1*CDL*((NDD1*MF*DrugRange1+NDD1*MF*CDD1*MF*DrugRange1-1*CDD1\hat{}2*MF-1*DrugRange1*CDD1)/(DrugRange1*CDD1))$$

To Calculate the Level/Response for the Second Agent $$NDL2=-1*NDL1*((NDD2*MF*DrugRange2+NDD2*MF*CDD2*MF*DrugRange2-1*CDD2\hat{}2*MF-1*DrugRange2*CDD2)/(DrugRange2*CDD2))$$

To Calculate the Level/Response for the Third Agent $$NDL3=-1*NDL2*((NDD3*MF*DrugRange3+NDD3*MF*CDD3*MF*DrugRange3-1*CDD3\hat{}2*MF-1*DrugRange3*CDD3)/(DrugRange3*CDD3))$$

wherein,
- NDL1=New First Drug Level
- NDL2=New Second Drug Level
- NDL3=New Third Drug Level
- CDL=Current Drug Level
- MarkerFunction1 (MF1)=1.5 ^ (CDL/MarkerRange)
- MarkerRange=The maximal range typically seen for marker.
- DrugRange1=The maximal range typically prescribed for the drug1
- DrugRange2=The maximal range typically prescribed for the drug2
- DrugRange3=The maximal range typically prescribed for the drug3

To Calculate the Proportion of Effect Based on the Amount of Agent and the Agent's Intrinsic Effect
- Agent1 Effect=1
- Agent2 Effect=1
- Agent3 Effect=1

$$Agent1 \ Proportion = \frac{Dose1/Range1}{(Dose1/Range1 + Dose2/Range2 + Dose3/Range3)}$$

$$Agent2 \ Proportion = \frac{Dose2/Range2}{(Dose1/Range1 + Dose2/Range2 + Dose3/Range3)}$$

$$Agent3 \ Proportion = \frac{Dose3/Range3}{(Dose1/Range1 + Dose2/Range2 + Dose3/Range3)}$$

$$FOE1 = \frac{Dose1/Range1}{(Dose1/Range1 + Dose2/Range2 + Dose3/Range3)} \times Agent1 \ Effect$$

$$FOE2 = \frac{Dose2/Range2}{(Dose1/Range1 + Dose2/Range2 + Dose3/Range3)} \times Agent2 \ Effect$$

$$FOE3 = \frac{Dose3/Range3}{(Dose1/Range1 + Dose2/Range2 + Dose3/Range3)} \times Agent3 \ Effect.$$

10. An apparatus for calculating the next best dose for each agent of a multi-agent therapy which a patient may be using and accounting for the level or degree of response that a patient has to each agent, comprising:
- first means for accepting as first inputs the patient's current doses for n number of agents which the patient may be using;
- second means for accepting as second inputs one or more numerical markers indicating one or more responses of the patient; and third means for calculating new agent doses for said n number of agents as a function of said first inputs, said second inputs, and contributions which each agent makes to an overall effect to be achieved by said multi-agent therapy, wherein said third means calculates said new agent doses as follows To Calculate the Range for the First Agent $$NAD1=CAD1+(\% \text{ change level First}/MF)/1+(CAD1/DrugRange1))*CAD1$$

To Calculate the Dose for the Second Agent $$NAD2=CAD2+(\% \text{ change level Second}/MF)/1+(CAD2/DrugRange2))*CAD2$$

To Calculate the Dose for the nth Agent $$NADn=CADn+(\% \text{ change level } nth/MF)/1+(CADn/DrugRangen))*CADn$$

wherein,

% change level First=(DDNM−CDNM)*FOE1/CDNM For regular markers

% change level First=(CDNM−DDNM)*FOE1/CDNM For inverse markers

% change level Second=(DDNM−CDNM)*FOE2/CDNM For regular markers

% change level Second=(CDNM−DDNM)*FOE2/CDNM For inverse markers

% change level nth=(DDNM−CDNM)*FOEn/CDNM For regular markers

% change level nth=(CDNM−DDNM)*FOEn/CDNM For inverse markers

CAD1=Current agent dose of the first agent

CAD2=Current agent dose of the second agent

CADn=Current agent dose of the nth agent

NAD1 high First=New first agent high dose range value

NAD2 high Second=New second agent high dose range value

NADn high Third=New nth agent high dose range value

CDNM1=Current agent numerical marker for the first agent

CDNM2=Current agent numerical marker for the second agent

CDNMn=Current agent numerical marker for the nth agent

DDNM1=Desired agent numerical marker for the first agent

DDNM2=Desired agent numerical marker for the second agent

DDNMn=Desired agent numerical marker for the nth agent

FOE1=Factor of effect the first agent has on its associated numerical marker

FOE2=Factor of effect the second agent has on its associated numerical marker

FOEn=Factor of effect the nth agent has on its associated numerical marker

To Calculate the Level/Response for the First Agent $$NDL1=-1*CDL*((NDD1*MF*DrugRange1+NDD1*MF*CDD1*MF*DrugRange1-1*CDD1\hat{\ }2*MF-1*DrugRange1*CDD1)/(DrugRange1*CDD1))$$

To Calculate the Level/Response for the Second Agent $$NDL2=-1*NDL1*((NDD2*MF*DrugRange2+NDD2*MF*CDD2*MF*DrugRange2-1*CDD2\hat{\ }2*MF-1*DrugRange2*CDD2)/(DrugRange2*CDD2))$$

To Calculate the Level/Response for the Third Agent $$NDLn=-1*NDLn1*((NDDn*MF*DrugRangen+NDDn*MFn*CDDn*MFn*DrugRangen-1*CDDn2\hat{\ }2*MFn-1*DrugRangen*CDDn)/(DrugRangen*CDDn))$$

wherein,

NDL1=New First Drug Level

NDL2=New Second Drug Level

NDL3=New Third Drug Level

CDL=Current Drug Level

MarkerFunction1 (MF1)=1.5 ^ (CDL/MarkerRange)

MarkerRange=The maximal range typically seen for marker.

DrugRange1=The maximal range typically prescribed for the drug1

DrugRange2=The maximal range typically prescribed for the drug2

DrugRange3=The maximal range typically prescribed for the drug3

To Calculate the Proportion of Effect Based on the Amount of Agent and the Agent's Intrinsic Effect Agent1 Effect=1

Agent2 Effect=1

Agent n Effect=1

$$Agent1\ Proportion = \frac{Dose1/Range1}{(Dose1/Range1 + Dose2/Range2 + \ldots\ Dose\ n/Range\ n)}$$

$$Agent2\ Proportion = \frac{Dose2/Range2}{(Dose1/Range1 + Dose2/Range2 + \ldots\ Dose\ n/Range\ n)}$$

$$Agent\ n\ Proportion = \frac{Dose\ n/Range\ n}{(Dose1/Range1 + Dose2/Range2 + \ldots\ Dose\ n/Range\ n)}$$

$$FOE1 = \frac{Dose1/Range1}{(Dose1/Range1 + Dose2/Range2 + \ldots\ Dose\ n/Range\ n)} \times Agent1\ Effect$$

$$FOE2 = \frac{Dose2/Range2}{(Dose1/Range1 + Dose2/Range2 + \ldots\ Dose\ n/Range\ n)} \times Agent2\ Effect$$

$$FOEn = \frac{(Dose\ n/Range\ n)}{(Dose1/Range1 + Dose2/Range2 + \ldots\ Dose\ n/Range\ n)} \times Agent\ n\ Effect.$$

* * * * *